US006391618B1

(12) United States Patent
Cheung (10) Patent No.: US 6,391,618 B1
(45) Date of Patent: May 21, 2002

(54) METHODS AND COMPOSITIONS FOR DEGRADING ENVIRONMENTAL TOXINS

(75) Inventor: Ling Yuk Cheung, Hong Kong (HK)

(73) Assignee: Ultra Biotech Limited (GB)

( * ) Notice: Subject to any disclaimer, the term of this patent is extended or adjusted under 35 U.S.C. 154(b) by 0 days.

(21) Appl. No.: 09/797,378

(22) Filed: Mar. 1, 2001

(51) Int. Cl.$^7$ ............................. C12N 1/14; C12N 13/00

(52) U.S. Cl. ............................... 435/255.1; 435/254.1; 435/173.1; 435/173.8; 435/254.21

(58) Field of Search ........................... 435/255.1, 173.1, 435/173.8, 254.21, 254.1

(56) References Cited

U.S. PATENT DOCUMENTS

| | | | |
|---|---|---|---|
| 4,081,367 A | 3/1978 | Hulls et al. | 210/610 |
| 4,183,807 A | 1/1980 | Yoshizawa et al. | 210/611 |
| 4,211,645 A | 7/1980 | Zajic et al. | 210/611 |
| 4,391,887 A * | 7/1983 | Baumgarten et al. | 435/42 |
| 4,559,305 A | 12/1985 | Zajic et al. | 435/243 |
| 4,816,158 A | 3/1989 | Shimura et al. | 210/610 |
| 5,075,008 A | 12/1991 | Chigusa et al. | 210/610 |
| 5,106,594 A | 4/1992 | Held et al. | 422/292 |
| 5,416,010 A | 5/1995 | Langenberg et al. | 435/468 |
| 5,476,787 A | 12/1995 | Yokoyama et al. | 435/262.5 |
| 5,567,314 A | 10/1996 | Chigusa et al. | 210/150 |
| 5,578,486 A | 11/1996 | Zhang | 435/243 |
| 5,707,524 A | 1/1998 | Potter | 210/606 |
| 5,879,928 A | 3/1999 | Dale et al. | 435/264 |
| 6,036,854 A | 3/2000 | Potter | 210/177 |

FOREIGN PATENT DOCUMENTS

| | | |
|---|---|---|
| CN | 1110317 A | 10/1995 |
| EP | 0041373 | 12/1981 |
| RU | 415983 A | 11/1974 |
| WO | WO 99/60142 | 11/1999 |

OTHER PUBLICATIONS

*Saccharomyces cerevisia* ex Hansen (http://www.im.ac.cn/database/yeast/y122.htm) and (http://www.im.ac.cn/database/catalogs.shtml) Apr. 24, 1996.*
K. Asami et al., "Real–Time Monitoring of Yeast Cell Division by Dielectric Spectroscopy", *Biophysical Journal*, 76, pp. 3345–3348 (1999).
E.K. Balcer–Kubiczek et al., "Expression Analysis of Human HL60 Cells Exposed to 60 Hz Square–or Sine–Wave Magnetic Fields", *Radiation Research*, 153, pp. 670–678 (2000).
C.A.L. Basset et al., "Beneficial Effects of Electromagnetic Fields", *Journal of Cellular Biochemistry*, 51, pp. 387–393 (1993).
P. Conti et al., "Effect of Electromagnetic Fields on Several CD Markers and Transcription and Expression of CD4", *Immunobiology*, 201, pp. 36–48 (1999).

A.M. Gonzalez et al., "Effects of an Electric Field of Sinusoidal Waves on the Amino Acid Biosynthesis by Azotobacter", *Z. Naturforsch*, 35, pp. 258–261 (1980).
E.M. Goodman et al., "Effects of Electromagnetic Fields on Molecules and Cells", *International Review of Cytology*, 158, pp. 279–339 (1995).
T. Grospietsch et al., "Stimulating Effects of Modulated 150 MHz Electromagnetic Fields on the Growth of *Escherichia coli* in a Cavity Resonator", *Bioelectrochemistry and Bioenergetics*, 37, pp. 17–23 (1995).
W. Grundler et al., "Nonthermal Effects of Millimeter Microwaves on Yeast Growth", *Z Naturforsch*, 33, pp. 15–22 (1978).
W. Grundler et al., "Mechanisms of Electromagnetic Interaction with Cellular System", *Naturwissenschaften*, 79, pp. 551–559 (1992).
O.I. Ivaschuk et al., "Exposure of Nerve Growth Factor–Treated PC12 Rat Pheochromocytoma Cells to a Modulator Radiofrequency Field at 836.55 MHz: Effects on c–jun and c–fos Expression", *Bioelectromagnetics*, 18, pp. 223–229 (1997).
F. Jelinek et al., "Microelectronic Sensors for Measurement of Electromagnetic Fields of Living Cells and Experimental Results", *Bioelectrochemistry and Bioenergetics*, 48, pp. 261–266 (1999).
A. Lacy–Hulbert et al., "Biological Responses to Electromagnetic Fields", *FASEB Journal*, 12, pp. 395–420 (1998).
C.R. Libertin et al., "Effects of Gamma Rays, Ultraviolet Radiation, Sunlight, Microwaves and Electromagnetic Fields on Gene Expression Mediated by Human Immunodeficiency Virus Promoter", *Radiation Research*, 140, pp. 91–96 (1994).
H. Lin et al., "Specific Region of the c–myc Promoter Is Responsive to Electric and Magnetic Fields", *Journal of Cellular Biochemistry*, 54, pp. 281–288 (1994).
H. Lin et al., "Magnetic Fields Activation of Protein–DNA Binding", *Journal of Cellular Biochemistry*, 70, pp. 297–303 (1998).
L.I. Loberg et al., "Expression of Cancer–Related Genes in Human Cells Exposed to 60 Hz Magnetic Fields", *Radiation Research*, 153, pp. 679–684 (2000).
R.L. Moore, "Biological Effects of Magnetic Fields: Studies with Microorganisms", *Canadian Journal of Microbiology*, 25, pp. 1145–1151 (1979).

(List continued on next page.)

Primary Examiner—Christopher R. Tate
(74) *Attorney, Agent, or Firm*—Fish & Neave; James F. Haley, Jr.; Z. Ying Li (57) ABSTRACT

Compositions comprising a plurality of yeast cells which have been cultured in the presence of an alternating electric field having a specific frequency and a specific field strength for a period of time sufficient to substantially increase the capability of said plurality of yeast cells to degrade environmental toxins, such as antibiotics and organic solvents, in a culture medium. Also included are methods of making such compositions.

74 Claims, 1 Drawing Sheet

OTHER PUBLICATIONS

C.A. Morehouse et al., "Exposure of Daudi Cells to Low–Frequency Magnetic Fields Does Not Elevate MYC Steady–State mRNA Levels", *Radiation Research*, 153, pp. 663–669 (2000).

V. Norris et al., "Do Bacteria Sing? Sonic Intercellular Communication Between Bacteria may Reflect Electromagnetic Intracellular Communication Involving Coherent Collective Vibrational Modes that Could Integrate Enzyme Activities and Gene Expression", *Molecular Microbiology*, 24, pp. 879–880 (1997).

G. Novelli et al., "Study of the Effects on DNA of Electromagnetic Fields Using Clamped Homogeneous Electric Field Gel Electrophoresis", *Biomedicine & Pharmacotherapy*, 45, pp. 451–454 (1991).

J.L. Phillips, "Effects of Electromagnetic Field Exposure on Gene Transcription", *Journal of Cellular Biochemistry*, 51, pp. 381–386 (1993).

V. Romano–Spica et al., "Ets1 Oncogene Induction by ELF–Modulated 50 MHz Radiofrequency Electromagnetic Field", *Bioelectromagnetics*, 21, pp. 8–18 (2000).

J.E. Trosko, "Human Health Consequences of Environmentally–Modulated Gene Expression: Potential Roles of ELF–EMF Induced Epigenetic Versus Mutagenic Mechanisms of Disease", *Bioelectromagnetics*, 21, pp. 402–406 (2000).

C. Ventura et al., "Elf–pulsed Magnetic Fields Modulate Opioid Peptide Gene Expression in Myocardial Cells", *Cardiovascular Research*, 45, pp. 1045–1064 (2000).

A.M. Woodward et al., "Genetic Programming as an Analytical Tool for Non–linear Dielectric Spectroscopy", *Bioelectrochemistry and Bioenergetics*, 48, pp. 389–396 (1999).

T. Yonetani et al., "Electromagnetic Properties of Hemoproteins", *The Journal of Biological Chemistry*, 247, pp. 2447–2455 (1972).

L. Zhang et al., "Electrostimulation of the Dehydrogenase System of Yeast by Alternating Currents", *Bioelectrochemistry and Bioenergetics*, 28, pp. 341–353 (1992).

* cited by examiner

METHODS AND COMPOSITIONS FOR DEGRADING ENVIRONMENTAL TOXINS

FIELD OF THE INVENTION

The invention relates to the use of yeast cells to degrade environmental toxins. These yeasts are useful in waste treatment, and can be obtained by growth in electromagnetic fields with specific frequencies and field strengths.

BACKGROUND OF THE INVENTION

Environmental pollution by urban sewage and industrial waste water has posed a serious health threat to living organisms in the world. Currently, the most common methods for large-scale water treatment include the activated sludge technology and the biomembrane technology. These technologies rely on the innate abilities of myriad natural microorganisms, such as fungi, bacteria and protozoa, to degrade pollutants. However, the compositions of these natural microbial components are difficult to control, affecting the reproducibility and quality of water treatment. Moreover, pathogenic microbes existing in these activated sludge or biomembranes cannot be selectively inhibited, and such microbes usually enter the environment with the treated water, causing "secondary pollution."

Further, most of the current technologies cannot degrade harmful chemicals such as pesticides, insecticides, and chemical fertilizers. These technologies also cannot alleviate eutrophication, another serious environmental problem around the world. Eutrophication is usually caused by sewage, industrial waste water, fertilizers and the like, It refers to waters (e.g., a lake or pond) rich in mineral and organic nutrients that promote a proliferation of plant life, especially algae, which reduces the dissolved oxygen content or otherwise deteriorates water quality. Eutrophication often results in the extinction of other organisms.

SUMMARY OF THE INVENTION

This invention is based on the discovery that certain yeast cells can be activated by electromagnetic fields having specific frequencies and field strengths to degrade or convert certain environmental pollutants, especially certain antibiotics and organic solvents, to environmentally harmless final products. Compositions comprising these activated yeast cells can therefore be useful for waste treatment, for example, for treatment of sewage, industrial waste water, surface water, drinking water, sediment, soil, garbage, and manure. Waste treatment methods using the compositions are more effective, efficient and economical than conventional methods.

Embraced within this invention is a composition comprising a plurality of yeast cells that have been cultured in an alternating electric field having a frequency in the range of about 70 to 100 MHz (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 MHz) and a field strength in the range of about 0.5 to 350 mV/cm (e.g., 30–220, 30–230, 30–250, 90–290, 80–280, 100–200, 110–280, 100–220, 116–225, 120–280, 90–190, 100–190, 160–300, 120–300, 200–300, or 130–310 mV/cm). The yeast cells are cultured in the alternating electric field for a period of time sufficient to substantially increase the capability of said plurality of yeast cells to degrade environmental toxins, such as antibiotics and organic solvents, in a culture medium. In one embodiment, the frequency and/or the field strength of the alternating electric field can be altered within the aforementioned ranges during said period of time. In other words, the yeast cells can be exposed to a series of electromagnetic fields. An exemplary period of time is about 12–400 hours, e.g., 180–328, 114–244, 80–380, 80–365, 120–350, 90–330, 130–330, 100–280, 110–330, 130–290, 80–290, 110–360, or 110–340 hours.

This invention also embraces a composition comprising a plurality of yeast cells that have been cultured in an alternating electric field having a frequency in the range of about 126 to 142 MHz (e.g., 126, 127, 128, 129, 130, 131, 132, 123, 134, 135, 136, 137, 138, 139, 140, 141, or 142 MHz) and a field strength in the range of about 0.5 to 350 mV/cm (e.g., 90–280 mV/cm) for a period of time sufficient to substantially increase the capability of said plurality of yeast cells to degrade trichloromethane in a culture medium.

This invention also embraces a composition comprising a plurality of yeast cells that have been cultured in an alternating electric field having a frequency in the range of about 52 to 70 MHz (e.g., 52, 53, 54, 55, 56, 57, 58, 59, 60, 61, 62, 63, 64, 65, 66, 67, 68, 69, or 70 MHz) and a field strength in the range of about 0.5 to 350 mV/cm (e.g., 80–280 mV/cm) for a period of time sufficient to substantially increase the capability Of said plurality of yeast cells to degrade toluene or ethylbenzene in a culture medium.

This invention also embraces a composition comprising a plurality of yeast cells that have been cultured in an alternating electric field having a frequency in the range of about 30 to 50 MHz (e.g., 30, 32, 34, 36, 38, 40, 42, 44, 46, 48, or 50 MHz) and a field strength in the range of about 0.5 to 350 mV/cm (e.g., 80–280 mV/cm) for a period of time sufficient to substantially increase the capability of said plurality of yeast cells to degrade p-xylene in a culture medium.

This invention embraces yet another composition comprising a plurality of yeast cells that have been cultured in an alternating electric field having a frequency in the range of about 200 to 220 MHz (e.g., 200, 201, 202, 203, 204, 205, 206, 207, 208, 209, 210, 211, 212, 213, 214, 215, 216, 217, 218, 219, or 220 MHz) and a field strength in the range of about 0.5 to 350 mV/cm (e.g., 80–280 mV/cm) for a period of time sufficient to substantially increase the capability of said plurality of yeast cells to degrade furazolidonum in a culture medium.

This invention embraces another composition comprising a plurality of yeast cells that have been cultured in an alternating electric field having a frequency in the range of about 213 to 229 MHz (e.g., 213, 214, 215, 216, 217, 218, 219, 220, 221, 222, 223, 224, 225, 226, 227, 228, or 229 MHz) and a field strength in the range of about 0.5 to 350 mV/cm (e.g., 90–280 mV/cm) for a period of time sufficient to substantially increase the capability of said plurality of yeast cells to degrade decoquinate in a culture medium.

This invention also embraces a composition comprising a plurality of yeast cells that have been cultured in an alternating electric field having a frequency in the range of about 133 to 151 MHz (e.g., 133, 134, 135, 136, 137, 138, 139, 140, 141, 142, 143, 144, 145, 146, 147, 148, 149, 150, or 151 MHz) and a field strength in the range of about 0.5 to 350 mV/cm (e.g., 120–280 mV/cm) for a period of time sufficient to substantially increase the capability of said plurality of yeast cells to degrade benzaldehyde in a culture medium.

This invention also embraces a composition comprising a plurality of yeast cells that have been cultured in an alternating electric field having a frequency in the range of about 145 to 162 MHz (e.g., 145, 146, 147, 148, 149, 150, 151, 152, 153, 154 155, 156, 157, 158, 159, 160, 161, or 162

MHz)and a field strength in the range of about 0.5 to 350 mV/cm (e.g., 100–200 mV/cm) for a period of time sufficient to substantially increase the capability of said plurality of yeast cells to degrade propylaldehyde in a culture medium.

This invention also embraces a composition comprising a plurality of yeast cells that have been cultured in an alternating electric geld having a frequency in the range of about 156 to 176 MHz (e.g., 156, 157, 158, 159, 160, 161, 162, 163, 164, 165, 166, 167, 168, 169, 170, 171, 172, 173, 174, 175, or 176 MHz) and a field strength in the range of about 0.5 to 350 mV/cm (e.g., 110–280 mV/cm) for a period of time sufficient to substantially increase the capability of said plurality of yeast cells to degrade enanthaldehyde in a culture medium.

This invention also embraces a composition comprising a plurality of yeast cells that have been cultured in an alternating electric field having a frequency in the range of about 163 to 183 MHz (e.g., 163, 164, 165, 166, 167, 168, 169, 170, 171, 172, 173, 174, 175, 176, 177, 178, 179, 180, 181, 182, or 183 MHz) and a field strength in the range of about 0.5 to 350 mV/cm (e.g., 100–220 mV/cm) for a period of time sufficient to substantially increase the capability of said plurality of yeast cells to degrade m-dichlorobenzene in a culture medium.

This invention embraces yet another composition comprising a plurality of yeast cells that have been cultured in an alternating electric field having a frequency in the range of about 175 to 191 MHz (e.g., 175, 176, 177, 178, 179, 190, 181, 182, 183, 184, 185, 186, 187, 188, 189, 190, or 191 MHz) and a field strength in the range of about 0.5 to 350 mV/cm (e.g., 116–225 mV/cm) for a period of time sufficient to substantially increase the capability of said plurality of yeast cells to degrade acetophenone in a culture medium.

This invention also embraces a composition comprising a plurality of yeast cells that have been cultured in an alternating electric field having a frequency in the range of about 183 to 205 MHz (e.g., 183, 184, 185, 186, 187, 188, 189, 190, 191, 192, 193, 194, 195, 196, 197, 198, 199, 200, 201, 202, 203, 204, or 205 MHz) and a field strength in the range of about 0.5 to 350 mV/cm (e.g., 90–190 mV/cm) for a period of time sufficient to substantially increase the capability of said plurality of yeast cells to degrade arsenic acid in a culture medium.

This invention also embraces a composition comprising a plurality of yeast cells that have been cultured in an alternating electric field having a frequency in the range of about 114 to 128 MHz (e.g., 114, 115, 116, 117, 118, 119, 120, 121, 122, 123, 124, 125, 126, 127, or 128 MHz) and a field strength in the range of about 0.5 to 350 mV/cm (e.g., 100–190 mV/cm) for a period of time sufficient to substantially increase the capability of said plurality of yeast cells to degrade roxarsone in a culture medium.

This invention embraces another composition comprising a plurality of yeast cells that have been cultured in an alternating electric field having a frequency in the range of about 244 to 264 MHz (e.g., 244, 245, 246, 247, 248, 249, 250, 251, 252, 253, 254, 255, 256, 257, 258, 259, 260, 261, 262, 263, or 264 MHz) and a field strength in the range of about 0.5 to 350 mV/cm (e.g., 160–300 mV/cm) for a period of time sufficient to substantially increase the capability of said plurality of yeast cells to degrade dodecane in a culture medium.

This invention also embraces a composition comprising a plurality of yeast cells that have been cultured in an alternating electric field having a frequency in the range of about 252 to 278 MHz (e.g., 252, 253, 254, 255, 256, 257, 258, 259, 260, 261, 262, 263, 264, 265, 266, 267, 268, 269, 270, 271, 272, 273, 274, 275, 276, 277, or 278 MHz) and a field strength in the range of about 0.5 to 350 mV/cm (e.g., 120–300 mV/cm) for a period of time sufficient to substantially increase the capability of said plurality of yeast cells to degrade nonadjacent or octacosane in a culture medium.

This invention also embraces a composition comprising a plurality of yeast cells that have been cultured in an alternating electric field having a frequency in the range of about 220 to 250 MHz (e.g., 220, 222, 224, 226, 228, 230, 232, 234, 236, 238, 240, 242, 244, 246, 248, or 250 MHz) and a field strength in the range of about 0.5 to 350 mV/cm (e.g., 200–300 mV/cm) for a period of time sufficient to substantially increase the capability of said plurality of yeast cells to degrade trichlorphonum in a culture medium.

This invention embraces yet another composition comprising a plurality of yeast cells that have been cultured in an alternating electric field having a frequency in the range of about 220 to 250 MHz (e.g., 220, 222, 224, 226, 228, 230, 232, 234, 236, 238, 240, 242, 244, 246, 248, or 250 MHz) and a field strength in the range of about 0.5 to 350 mV/cm (e.g., 130–310 mV/cm) for a period of time sufficient to substantially increase the capability of said plurality of yeast cells to degrade dinitomidum or zoalene in a culture medium.

Yeast cells that can be included in this composition can all be obtained from the China General Microbiological Culture Collection Center ("CGMCC"), a depository recognized under the Budapest Treaty (China Committee for Culture Collection of Microorganisms, Institute of Microbiology, Chinese Academy of Sciences, Haidian, P.O. BOX 2714, Beijing, 100080, China). Useful yeast species include, but are not limited to, *Saccharomyces cerevisiae, Saccharomyces carlsbergensis, Saccharomyces rouxii,* and *Candida utilis.* For instance, the yeast cells can be of the strain *Saccharomyces cerevisiae* AS2.4, AS2.14, AS2.416, AS2.430, AS2.593, IFFI1002, IFFI1006, IFFI1043, IFFI1045, IFFI1048, IFFI1063, IFFI1059, IFFI1206, IFFI1209, IFFI1210, IFFI1211, IFFI1213, IFFI1215, IFFI1220, IFFI1221, IFFI1224, IFFI1248, IFFI1270, IFFI1290, IFFI1291, IFFI1293, IFFI1297, IFFI1301, IFFI1302, IFFI1310, IFFI1311, IFFI1331, IFFI1335, IFFI1336, IFFI1338, IFFI1339, IFFI1340, IFFI1345, IFFI1396, IFFI1399, IFFI1411, or IFFI1413; *Saccharomyces willianus* Saccardo AS2.293; *Saccharomyces carlsbergensis* AS2.377 or AS2.444; *Saccharomyces rouxii* AS2.178; or *Candida utilis* AS2.120.

This invention also embraces a composition comprising a plurality of yeast cells, wherein said plurality of yeast cells have been activated such that they have a substantially increased capability to degrade environmental toxins, such as antibiotics or other organic compounds of interests, in a culture medium as compared to unactivated yeast cells. Included within this invention are also methods of making these compositions.

As used herein, "substantially increase" means an increase of more than 10 (e.g., $10^2$, $10^3$, $10^4$, $10^5$, or $10^6$) fold.

A "culture medium" refers to a medium used in a laboratory for selecting and growing a given yeast strain, or to water in need of treatment.

Antibiotics degradable by the yeast compositions of the invention include, but are not limited to, beta-lactams, tetracyclines, polypeptides, glycopeptides, aminoglycosides, and macrolides. Specific examples of antibiotics are penicillin, aureomycin, chlotetracycline, oxytetracycline, doxycycline, tetracycline, streptomycin, kanamycin, erythromycin, spiramycin, and bacitracin. Organic solvents degradable by the yeast compositions of this invention include, but are not limited to, trichloromethane, toluene, ethylbenzene, p-xylene, furazolidonum, decoquinate, benzaldehyde, propylaldehyde, enanthaldehyde, m-dichlorobenzene, acetophenone, arsanilic acid, roxarsone, dodecane, nonadecane, octacosane, trichlorophonum, dinitomidum and zoalene.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

DETAILED DESCRIPTION OF THE INVENTION

This invention is based on the discovery that certain yeast strains can be activated by electromagnetic fields ("EMF") having specific frequencies and field strengths to become highly efficient in degrading certain toxic chemicals such as antibiotics used in fodder, and organic solvents. Yeast cells having this function are defined herein as belonging to the same "functional group." Compositions containing the activated yeast cells are useful in waste treatment.

Without being bound by any theory or mechanism, the inventor believes that EMFs activate or enhance the expression of a gene or a set of genes in the yeast cells such that the yeast cells become active or more efficient in performing certain metabolic activities which lead to the desired degradation result.

I. Yeast Strains Useful in the Invention

The types of yeasts useful in this invention include, but are not limited to, yeasts of the genera of Saccharomyces, Schizosaccharomyces, Sporobolomyces, Torulopsis, Trichosporon, Wickerhamia, Ashbya, Blastomyces, Candida, Citeromyces, Crebrothecium, Cryptococcus, Debaryomyces, Endomycopsis, Eremothecium, Geotrichum, Hansenula, Kloeckera, Lipomyces, Pichia, Rhodosporidium, and Rhodotorula.

Exemplary species within the above-listed genera include, but are not limited to, *Saccharomyces cerevisiae, Saccharomyces bailii, Saccharomyces carlsbergensis, Saccharomyces chevalieri, Saccharomyces delbrueckii, Saccharomyces exiguus, Saccharomycesfermentati, Saccharomyces logos, Saccharomyces mellis, Saccharomyces microellipsoides, Saccharomyces oviformis, Saccharomyces rosei, Saccharomyces rouxii, Saccharomyces sake, Saccharomyces uvarum, Saccharomyces willianus,* Saccharomyces sp., *Saccharomyces ludwigii, Saccharomyces sinenses, Saccharomyces bailii, Saccharomyces carlsbergensis, Schizosaccharomyces octosporus, Schizosaccharomyces pombe, Sporobolomyces roseus, Sporobolomyces salmonicolor, Torulopsis candida, Torulopsis famta, Torulopsis globosa, Torulopsis inconspicua, Trichosporon behrendoo, Trichosporon capitatum, Trichosporon cutaneum, Wickerhamia fluoresens, Ashbya gossypii, Blastomyces dermatitidis, Candida albicans, Candida arborea, Candida guilliermondii, Candida krusei, Candida lambica, Candida lipolytica, Candida parakrusei, Candida parapsilosis, Candida pseudotropicalis, Candida pulcherrima, Candida robusta, Candida rugousa, Candida tropicalis, Candida utilis, Citeromyces matrilensis, Crebrothecium ashbyii, Cryptococcus laurentii, Cryptococcus neoformans, Debaryomyces hansenii, Debaryomyces kloeckeri,* Debaryomyces sp., *Endomycopsis fibuligera, Eremothecium ashbyii, Geotrichum candidum, Geotrichum ludwigii, Geotrichum robustum, Geotrichum suaveolens, Hansenula anomala, Hansenula arabitolgens, Hansenula jadinii, Hansenula saturnus, Hansenula schneggii, Hansenula subpelliculosa, Kloeckera apiculata, Lipomyces starkeyi, Pichiafarinosa, Pichia membranaefaciens, Rhodosporidium toruloides, Rhodotorula aurantiaca, Rhodotorula glutinis, Rhodotorula minuta, Rhodotorula rubar,* and *Rhodotorula sinesis.*

Yeast gtraing useful in this invention can be obtained from laboratory cultures, or from publically accessible culture depositories, such as CGMCC and the American Type Culture Collection, 10801 University Boulevard, Manassas, Va. 20110-2209. Non-limiting examples of useful strains (with the accession numbers of CGMCC) are *Saccharomyces cerevisiae* AS2.4, AS2.14, AS2.416, AS2.430, AS2.593, IFFI1002, IFFI1006, IFFI1043, IFFI1045, IFFI1048, IFFI1063, IFFI1059, IFFI1206, IFFI1209, IFFI1210, IFFI1211, IFFI1213, IFFI1215, IFFI1220, IFFI1221, IFFI1224, IFFI1248, IFFI1270, IFFI1290, IFFI1291, IFFI1293, IFFI1297, IFFI1301, IFFI1302, IFFI1310, IFFI1311, IFFI1331, IFFI1335, IFFI1336, IFFI1338, IFFI1339, IFFI1340, IFFI1345, IFFI1396, IFFI1399, IFFI1411, and IFFI1413, *Saccharomyces willianus* Saccardo AS2.293, *Saccharomyces carlsbergensis* AS2.377 and AS2.444; *Saccharomyces rouxii* AS2.178; and *Candida utilis* AS2.120.

Although it is preferred, the preparation of the yeast compositions of this invention is not limited to starting with a pure strain of yeast. A yeast composition of the invention may be produced by culturing a mixture of yeast cells of different species or strains that have the same function. The ability of any species or strain of yeast to perform this function can be readily tested by methods known in the art. See also discussions below.

Certain yeast species that can be activated according to the present invention are known to be pathogenic to human and/or other living organisms These yeast species include, for example, *Ashbya gossypii, Blastomyces dermatitidis, Candida albicans, Candida parakrusei, Candida tropicalis, Citeromyces matritensis, Crebrothecium ashbyii, Cryptococcus laurentii, Cryptococcus neoformans, Debaryomyces hansenii, Debaryomyces kloeckeri,* Debaryomyces sp., and *Endomycopsis fibuligera.* Under certain circumstances, it may be less preferable to use such pathogenic yeasts in this invention. Ifuse of these species is necessary, caution should be exercised to minimize the leak of the yeast cells into the final treatment product that enters the environment.

II. Application of Electromagnetic Fields

An electromagnetic field ugefiul in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag—AgCl electrodes in solutions rich in chloride ions, and run at as low a voltage as possible. For general review, see Goodman et al., *Effects of EMF on Molecules and Cells,* International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from 5 MHz to 1000 MHz, e.g., 70–100, 126–142, 52–70, 30–50, 200–220, 213–229, 133–151, 145–162, 156–176, 163–183, 175–191, 183–205, 114–128, 244–264, 252–278, or 220–250 MHz. Exemplary frequencies are 70, 72, 74, 76, 78, 80, 82, 84, 86, 88, 90, 92, 94, 96, 98, or 100 MHz. The field strength of the electric field useful in this invention ranges from about 0.5 to 350 mV/cm, for example, from about 20–320 mV/cm (e.g., 30–220, 30–230, 30–250, 90–280, 80–280, 100–200, 110–280, 100–220, 116–225, 120–290, 90–190, 100–190, 160–300, 120–100, 200–300, or 130–310 mV/cm). Exemplary field strengths are 48, 89, 93, 98, 103, 107, 110, 112, 124, 126, 130, 133, 138, 168, 200, 202, 213, 219, and 274 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength, or a different frequency and a different field strength. Such frequencies and field strengths are preferably within the above-described ranges. In one embodiment, an EMF at the beginning of the series has a field strength identical to or lower than that of a subsequent EMF, such that the yeast cell culture is exposed to EMFs of progressively increasing field strength. Although any practical number of EMEs can be used in a series, it may be preferred that the yeast culture be exposed to a total of 2, 3, 4, 5, 6, 7, 8, 9 or 10 EMFs in a series.

By way of example, the yeast cells can be first cultured in a series of alternating electric fields each having a frequency in the range of 70 to 100 MHz and a field strength in the range of 20 to 320 mV/cm. The yeast cells are exposed to each EMF for about 10 to 25 hours. After culturing in the first series of EMFs, the resultant yeast cells are fuirther incubated in a second series of alternating electric fields for a total of 30 to 120 hours. It may be preferred that the frequencies in the second series of alternating electric fields are identical to those of the first series in sequence and the field strengths in the second series are increased to a higher level within the range of 20 to 320 mV/cm.

Alternatively, the yeast cells can be cultured in a series of alternating electric fields each having a frequency in the range of 70 to 100 MHz and a field strength in the range of 20 to 320 mV/cm. The yeast cells are exposed to each ENT for about 20 to 40 hours. Preferably, the field strength remains the same in the series whereas the frequency progressively increases.

In another embodiment, the yeast cells can be cultured in a first series of alternating electric fields each having a frequency in the range of 126–142, 52–70, 30–50, 200–220, 213–229, 133–151, 145–162, 156–176, 163–183, 175–191, 183–205, 114–128, 244–264, 252–278, or 220–250 MHz and a field strength in the range of 90–280, 80–280, 120–280, 100–200, 110–280, 100–220, 116–225, 90–190, 100–190, 160–300, 120–300, 200–300, or 130–310 mV/cm. The yeast cells are exposed to each EMF for about 10 to 25 hours. After culturing in the first series of EMFs, the resultant yeast cells are further incubated in a second series of alternating electric fields for a total of 30 to 120 hours. It may be preferred that the electric field frequencies in this second series are identical to those in the first series while the field strengths in the second series are increased to a higher level within the above-described ranges. Alternatively, the yeast cells can be cultured in a series of alternating electric fields each having a frequency in the range of 126–142, 52–70, 30–50, 200–220, 213–229, 133–151, 145–162, 156–176, 163–183, 175–191, 183–205, 114–128, 244–264, 252–278, or 220–250 MHz and a field strength in the range of 90–280, 80–280, 120–280, 100–200, 110–280, 100–220, 116–225, 90–190, 100–190, 160–300, 120–300, 200–300, or 130–310 mV/cm. The yeast cells are exposed to each EMF for about 20 to 40 hours. Preferably, the field strength remains the same in the series whereas the frequency progressively increases.

Although the yeast cells can be activated after even a few hours of culturing in the presence of an EMF, it may be preferred that the activated yeast cells be allowed to multiply and grow in the presence of the EMF(s) for a total of 180–328, 114–244, 80–380, 80–365, 120–350, 90–330, 130–330, 100–280, 110–330, 130–290, 80–290, 110–360, or 110–340 hours.

Figure 1:
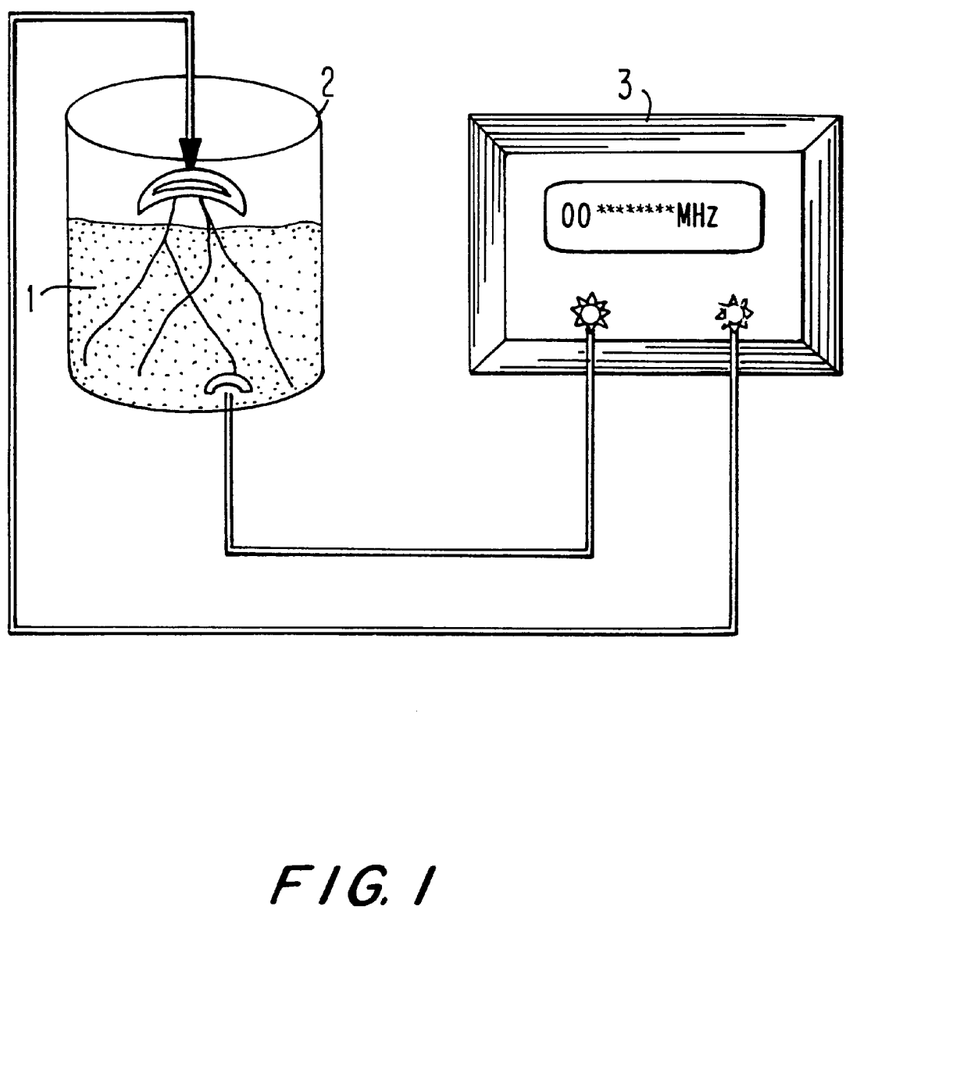
FIG. 1 is a schematic diagram showing an exemplary apparatus for activating yeast cells using electromagnetic fields. 1: yeast culture; 2: container; 3: power supply.

FIG. 1 illustrates an exemplary apparatus for generating alternating electric fields. An electric field of a desired frequency and intensity is generated by an AC source (3) capable of generating an alternating electric field, preferably in a sinusoidal wave form, in the frequency range of 5 to 1000 MHz. Signal generators capable of generating signals with a narrower frequency range can also be used. If desirable, a signal amplifier can also be used to increase the output. The alternating electric field can be applied to the culture by a variety of means including placing the yeast culture in close proximity to the signal emitters. In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy. The number of electrode wires used depends on the volume of the culture as well as the diameter of the wires. In a preferred embodiment, for a culture having a volume up to 5000 ml, one electrode wire having a diameter of 0.1 to 1.2 mm can be used for each 100 ml of culture. For a culture having a volume greater than 1000 L, one electrode wire having a diameter of 3 to 30 mm can be used for each 1000 L of culture.

III. Culture Media

Culture media useful in this invention contain sources of nutrients assimilable by yeast cells. In this invention, a culture medium refers to a laboratory culture medium or the liquid or solid waste in need of treatment. Complex carbon-containing substances in a suitable form (e.g., carbohydrates such as sucrose, glucose, dextrose, maltose and xylose; or coal) can be the carbon sources for yeast cells. In a laboratory culture medium, the exact quantity of the carbon sources can be adjusted in accordance with the other ingredients of the medium. In general, the amount of carbohydrate varies between about 0.1% and 5% by weight of the medium and preferably between about 0.1% and 2%, and most preferably about 1%. These carbon sources can be used individually or in combination. Among the inorganic salts which can be added to a laboratory culture medium are the customary salts capable of yielding sodium, potassium, calcium, phosphate, sulfate, carbonate, and like ions. Non-limiting examples of nutrient inorganic salts are $(NH_4)_2HPO_4$, $CaCO_3$, $KH_2PO_4$, $MgSO_4$, $NaCl$, and $CaSO_4$.

IV. Electromagnetic Activation of Yeast Cells

The yeast compositions of the invention can degrade environmentally harmful toxins, e.g., chemical compounds such as fertilizers, organic solvents, detergents, and antibiotics, into harmless simple molecules. These compositions are most efficient in degrading compounds having a molecular weight of 180 to 28,000 daltons.

To activate the innate ability of yeast cells to degrade environmental toxins, the cells can be cultured in an appropriate medium under sterile conditions at 25° C.–30° C. (e.g., 28° C.) for a sufficient amount of time, e.g., 12–400 hours (e.g., 180–328, 114–244, 80–380, 80–365, 120–350, 90–330, 130–330, 100–280, 110–330, 130–290, 80–290, 110–360, or 110–340 hours), in an alternating electric field or a series of alternating electric fields as described above The culturing process may preferably be conducted under conditions in which the concentration of dissolved oxygen is between 0.025 to 0.8 $mol/m^3$, preferably 0.4 $mol/m^3$. The oxygen level can be controlled by, for example, stirring and/or bubbling.

An exemplary medium contains in per 400 ml of sterile water: 8 g of sludge, 0.2 g of NaCl, 0.2 g of $MgSO_4.7H_2O$, 0.5 g of $CaCO_3.5H_2O$, 0.2 g of $CaSO_4.2H_2O$, 0.5 g of $K_2HPO_4$, 1.5 g of peptone, and 600 ml of sludge extract. The sludge extract is prepared as follows: 500 g of sludge known to be polluted by harmful chemicals is mixed and incubated with 600 ml of sterile water at 30–37° C. for 24 hours. The sludge mix is then filtered to obtain sludge extract. Subsequently, the yeast cells can be measured for their ability to degrade the various chemicals using standard methods.

Essentially the same protocol as described above can be used to grow activated yeast cells. To initiate the process, each 100 ml of culture medium is inoculated with CH yeast cells at a density of $10^2–10^5$ cells/ml, preferably $3\times10^2–10^4$ cells/ml. The culturing process is carried out at about 20–40° C., preferably at about 25–28° C., for 48–96 hours. The process can be scaled up or down according to needs. For an industrial scale of production, seventy-five liters of a sterile culture medium are inoculated with the yeast cells. This culture medium consists of 10 L of the culture medium described above for this particular yeast functional group, 30 kg of starch, and 65 L of distilled water. At the end of the culturing process, the yeast cells may preferably reach a concentration of $2\times10^{10}$ cells/ml. The cells are recovered from the culture by various methods known in the art, and stored at about 15–20° C. The yeast should be dried within 24 hours and stored in powder form.

V. Acclimatization of Yeast Cells to Waste Environment

In yet another embodiment of the invention, the yeast cells may also be cultured under certain conditions so as to acclimatize the cells to a particular type of waste. This acclimatization process results in better growth and survival of the yeasts in a particular waste environment.

To achieve this, the yeast cells of a given functional group are mixed with waste from a particular source at $10^6$ to $10^8$ cells (e.g., $10^7$ cells) per 1000 ml. The yeast cells are then exposed to an alternating electric field as described above. The strength of the electric field can be about 100 to 400 mV/cm (e.g., 120–250 mV/cm). The culture is incubated at temperatures that cycle between about 5° C. to about 45° C. at a 5° C. increment. For example, in a typical cycle, the temperature of the culture may start at 5° C. and be kept at this temperature for about 1–2 hours, then adjusted up to 10° C. and kept at this temperature for 1–2 hours, then adjusted to 15° C. and kept at this temperature for about 1–2 hours, and so on and so forth, until the temperature reaches 45° C. Then the temperature is brought down to 40° C. and kept at this temperature for about 1–2 hours, and then to 35° C. and kept at this temperature for about 1–2 hours, and so on and so forth, until the temperature returns to 5° C. The cycles are repeated for about 48–96 hours. The resulting yeast cells are then dried and stored at 0–4° C.

VI. Manufacture of the Waste Treatment Compositions

The yeast cells of this invention can be mixed with an appropriate filler, such as powder and coal ash at the following ratio: 600 L of mixed yeast cell culture at $2\times10^{10}$ cells/ml and 760 kg of filler materials. The mixture is quickly dried at a temperature below 65° C. for 10 minutes in a dryer, and then further dried at a temperature below 70° C. for no more than 30 minutes, go that the water content is less than 7%. The dried composition is then cooled to room temperature for packaging.

These dried yeast compositions may be used to treat polluted surface water, sewage, or any other type of solid or liquid waste. By way of example, to treat polluted surface water, a yeast solution may be prepared by adding 1 kg of the dried yeast composition to 30 L of clean water. The yeast solution is then sprayed onto the polluted surface water at about 1–3 L of the solution per square meter of the polluted surface water. To treat sewage or any other type of waste water, a yeast solution may be prepared by adding about 1 kg of the dried yeast composition to 10–30 L of clean water. The yeast solution is incubated at 10–35° C. for 24–48 hours. The resultant yeast solution is then added to the waste water at about 3–20 L of the solution per liter of waste water.

VII. EXAMPLES

The following examples are meant to illustrate the methods and materials of the present invention. Suitable modifications and adaptations of the described conditions and parameters which are obvious to those skilled in the art are within the spirit and scope of the present invention.

Example 1

Degradation of Penicillin

*Saccharomyces willianus* Saccardo AS2.293 cells were cultured in the presence of a series of alternating electric fields in the following sequence: the yeast cells were exposed to (1) an alternating electric field having a frequency of 77 MHz and a field strength of 48 mV/cm for 15 hours; (2) then to an alternating electric field having a frequency of 83 MHz and a field strength of 48 mV/cm for 15 hours; (3) then to an alternating electric field having a frequency of 90 MHz and a field strength of 48 mV/cm for 15 hours; (4) then to an alternating electric field having a frequency of 96 MHz and a field strength of 48 mV/cm for 15 hours, (5) then to an alternating electric field having a frequency of 77 MHz and a field strength of 200 mV/cm for 30 hours; (6) then to an alternating electric field having a frequency of 83 MHz and a field strength of 200 mV/cm for 30 hours; (7) then to an alternating electric field having a frequency of 90 MHz and a field strength of 200 mV/cm for 30 hours; and (8) finally to an alternating electric field having a frequency of 96 MHz and a field strength of 200 mV/cm for 30 hours.

To test the ability of the EMF-treated AS2.293 cells to degrade penicillin, waste water from a hospital was supplemented with procainpenzyl penicillin (or cloxacillin) to reconstitute a solution containing penicillin at 100 mg/L. 0.1 ml of the EMF-treated AS2.293 cells at a concentration higher than $10^8$ cells/ml was added to 100 L of the penicillin solution and cultured at 28° C. for 24 hours (solution A). One hundred liters of the penicillin solution containing the same number of non-treated cells (solution B) or containing no cells (solution C) were used as controls. After 24 hours of incubation, the penicillin solutions were examined using HPLC. The results showed that after 24 hours of incubation, the penicillin concentration of solution A decreased more than 23% relative to solution C. In contrast, the penicillin concentration of solution B showed no significant change relative to solution C.

Example 2

Degradation of Aureomycin

Saccharomyces cerevisiae Hansen IFFI1063 cells were cultured in the presence of a series of alternating electric fields in the following sequence: the yeast cells were exposed to (1) an alternating electric field having a frequency of 70 MHz and a field strength of 48 mV/cm for 15 hours; (2) then to an alternating electric field having a frequency of 73 MHz and a field strength of 48 mV/cm for 15 hours; (3) then to an alternating electric field having a frequency of 88 MHz and a field strength of 48 mV/cm for 15 hours; (4) then to an alternating electric field having a frequency of 98 MHz and a field strength of 48 mV/cm for 15 hours; (5) then to an alternating electric field having a frequency of 70 MHz and a field strength of 200 mV/cm for 30 hours; (6) then to an alternating electric field having a frequency of 73 MHz and a field strength of 200 mV/cm for 30 hours; (7) then to an alternating electric field having a frequency of 8 MHz and a field strength of 200 mV/cm for 30 hours; and (8) finally to an alternating electric field having a frequency of 98 MHz and a field strength of 200 mV/cm for 30 hours.

To test the ability of the EMF-treated IFFI1063 cells to degrade aureomycin, waste water from a hospital was supplemented with chlortetracycline hydrochloride (one type of aureomycin) to reconstitute a solution containing the antibiotics at 100 mg/L. 0.1 ml of the EMF-treated IFFI1063 cells at a concentration higher than $10^8$ cells/ml was added to 100 L of the antibiotics solution and cultured at 28° C. for 24 hours (solution A). One hundred liters of the antibiotics solution containing the same number of non-treated cells (solution B) or containing no cells (solution C) were used as controls. After 24 hours of incubation, the antibiotics solutions were examined using HPLC. The results showed that after 24 hours of incubation, the chlortetracycline hydrochloride concentration of solution A decreased more than 31% relative to solution C. In contrast, the chlortetracycline hydrochloride concentration of solution B showed no significant change relative to solution C.

Example 3

Degradation of Oxytetracycline

Saccharomyces cerevisiae Hansen IFFI1211 cells were cultured in the presence of a series of alternating electric fields in the following sequence: the yeast cells were exposed to (1) an alternating electric field having a frequency of 70 MHz and a field strength of 48 mV/cm for 15 hours; (2) then to an alternating electric field having a frequency of 74 MMz and a field strength of 48 mV/cm for 15 hours; (3) then to an alternating electric field having a frequency of 88 MHz and a field strength of 44 mV/cm for 15 hours; (4) then to an alternating electric field having a frequency of 98 MHz and a field strength of 48 mV/cm for 15 hours; (5) fin then to an alternating electric field having a frequency of 70 MHz and a field strength of 200 mV/cm for 30 hours; (6) then to an alternating electric field having a frequency of 74 MHz and a field strength of 200 mV/cm for 30 hours; (7) then to an alternating electric field having a frequency of 88 MHz and a field strength of 200 mV/cm for 30 hours; and (8) finally to an alternating electric field having a frequency of 98 MHz and a field strength of 200 mV/cm for 30 hours.

To test the ability of the EMF-treated IFFI1211 cells to degrade oxytetracycline ("OTC"), waste water from a hospital was supplemented with oxytetracycline hydrochloride to reconstitute a solution containing the antibiotics at 100 mg/L. 0.1 ml of the EMF-treated IFFI1211 cells at a concentration higher than $10^8$ cells/ml was added to 100 L of the antibiotics solution and cultured at 28° C. for 24 hours (solution A). One hundred liters of the antibiotics solution containing the same number of non-treated cells (solution B) or containing no cells (solution C) were used as controls. After 24 hours of incubation, the antibiotics solutions were examined using HPLC. The results showed that after 24 hours of incubation, the OTC concentration of solution A decreased more than 28% relative to solution C. In contrast, the OTC concentration of solution B showed no significant change relative to solution C.

Example 4

Degradation of Doxytetracycline

Saccharomyces cerevisiae Hansen IFFI1340 cells were cultured in the presence of a series of alternating electric fields in the following sequence: the yeast cells were exposed to (1) an alternating electric field having a frequency of 71 MHz and a field strength of 48 mV/cm for 15 hours; (2) then to an alternating electric field having a frequency of 73 MHz and a field strength of 48 mV/cm for 15 hours; (3) then to an alternating electric field having a frequency of 77 MHz and a field strength of 48 mV/cm for 15 hours; (4) then to an alternating electric field having a frequency of 88 MHz and a field strength of 48 mV/cm for 15 hours; (5) then to an alternating electric field having a frequency of 71 MHz and a field strength of 200 mV/cm for 30 hours; (6) then to an alternating electric field having a frequency of 73 MHz and a field strength of 200 mV/cm for 30 hours; (7) then to an alternating electric field having a frequency of 77 MHz and a field strength of 200 mV/cm for 30 hours; and (8) finally to an alternating electric field having a frequency of 88 MHz and a field strength of 200 mV/cm for 30 hours.

To test the ability of the EMF-treated IFFI1340 cells to degrade doxycycline ("DOTC"), waste water from a hospital was supplemented with DOTC to reconstitute a solution containing the antibiotics at 100 mg/L. 0.1 ml of the EMF-treated IFFI1340 cells at a concentration higher than $10^8$ cells/ml was added to 100 L of the antibiotics solution and cultured at 28° C. for 24 hours (solution A), One hundred liters of the antibiotics solution containing the same number of nontreated cells (solution B) or containing no cells (solution C) were used as controls. After 24 hours of incubation, the antibiotics solutions were examined using HPLC. The results showed that after 24 hours of incubation, the DOTC concentration of solution A decreased more than 33% relative to solution C. In contrast, the DOTC concentration of solution B showed no significant change relative to solution C.

Example 5
Degradation of Tetracycline

*Saccharomyces cerevisiae* Hansen IFFI1215 cells were cultured in the presence of a series of alternating electric fields in the following sequence: the yeast cells were exposed to (1) an alternating electric field having a frequency of 70 MHz and a field strength of 48 mV/cm for 15 hours; (2) then to an alternating electric field having a frequency of 75 MHz and a field strength of 48 mV/cm for 15 hours; (3) then to an alternating electric field having a frequency of 82 MHz and a field strength of 48 mV/cm for 15 hours; (4) then to an alternating electric field having a frequency of 85 MHz and a field strength of 48 mV/cm for 15 hours; (5) then to an alternating electric field having a frequency of 70 MHz and a field strength of 200 mV/cm for 30 hours; (6) then to an alternating electric field having a frequency of 75 MHz and a field strength of 200 mV/cm for 30 hours; (7) then to an alternating electric field having a frequency of 82 MHz and a field strength of 200 mV/cm for 30 hours; and (8) finally to an alternating electric field having a frequency of 85 MHz and a field strength of 200 mV/cm for 30 hours.

To test the ability of the EMF-treated IFFI1215 cells to degrade tetracycline ("TC"), waste water from a hospital was supplemented with TC to reconstitute a solution containing the antibiotics at 100 mg/L. 0.1 ml of the EMF-treated IFFI1215 cells at a concentration higher than $10^8$ cells/ml was added to 100 L of the antibiotics solution and cultured at 28° C for 24 hours (solution A). One hundred liters of the antibiotics solution containing the same number of non-treated cells (solution B) or containing no cells (solution C) were used as controls. After 24 hours of incubation, the antibiotics solutions were examined using HPLC. The results showed that after 24 hours of incubation, the TC concentration of solution A decreased more than 26% relative to solution C. In contrast, the TC concentration of solution B showed no significant change relative to solution C.

Example 6
Degradation of Streptomycin

*Saccharomyces cerevisiae* Hansen IFFI1213 cells were cultured in the presence of a series of alternating electric fields in the following sequence; the yeast cells were exposed to (1) an alternating electric field having a frequency of 70 MHz and a field strength of 48 mV/cm for 15 hours; (2) then to an alternating electric field having a frequency of 73 MHz and a field strength of 48 mV/cm for 15 hours; (3) then to an alternating electric field having a frequency of 80 MHz and a field strength of 48 mV/cm for 15 hours; (4) then to an alternating electric field having a frequency of 96 MHz and a field strength of 48 mV/cm for 15 hours; (5) then to an alternating electric field having a frequency of 70 MHz and a field strength of 200 mV/cm for 30 hours; (6) then to an alternating electric field having a frequency of 73 MHz and a field strength of 200 mV/cm for 30 hours; (7) then to an alternating electric field having a frequency of 80 MHz and a field strength of 200 mV/cm for 30 hours; and (8) finally to an alternating electric field having a frequency of 96 MHz and a Geld strength of 200 mV/cm for 30 hours.

To test the ability of the EMF-treated IFFI1213 cells to degrade streptomycin, waste water from a hospital was supplemented with streptomycin to reconstitute a solution containing the antibiotics at 100 mg/L. 0.1 ml of the EMF-treated IFFI1213 cells at a concentration higher than $10^8$ cells/ml was added to 100 L of the antibiotics solution and cultured at 28° C. for 24 hours (solution A). One hundred liters of the antibiotics solution containing the same number of non-treated cells (solution B) or containing no cells (solution C) were used as controls. After 24 hours of incubation, the antibiotics solutions were examined using HPLC. The results showed that after 24 hours of incubation, the streptomycin concentration of solution A decreased more than 31% relative to solution C. In contrast, the streptomycin concentration of solution B showed no significant change relative to solution C.

Example 7
Degradation of Kanamycin

*Saccharomyces cerevisiae* Hansen IFFI1206 cells were cultured in the presence of a series of alternating electric fields in the following sequence; the yeast cells were exposed to (1) an alternating electric field having a frequency of 71 MHz and a field strength of 48 mV/cm for 15 hours; (2) then to an alternating electric field having a frequency of 78 MHz and a field strength of 48 mV/cm for 15 hours; (3) then to an alternating electric field having a frequency of 86 MHz and a field strength of 48 mV/cm for 15 hours; (4) then to an alternating electric field having a frequency of 98 MHz and a field strength of 48 mV/cm for 15 hours; (5) then to an alternating electric field having a frequency of 71 MHz and a field strength of 200 mV/cm for 30 hours; (6) then to an alternating electric field having a frequency of 78 MHz and a field strength of 200 mV/cm for 30 hours; (7) then to an alternating electric field having a frequency of 86 MHz and a field strength of 200 mV/cm for 30 hours; and (8) finally to an alternating electric field having a frequency of 98 MHz and a field strength of 200 mV/cm for 30 hours.

To test the ability of the EMF-treated IFFI1206 cells to degrade kanamycin, waste water from a hospital was supplemented with kanamycin to reconstitute a solution containing the antibiotics at 100 mg/L. 0.1 ml of the EMF-treated IFFI1206 cells at a concentration higher than $10^8$ cells/ml was added to 100 L of the antibiotics solution and cultured at 28° C. for 24 hours (solution A). One hundred liters of the antibiotics solution containing the same number of non-treated cells (solution B) or containing no cells (solution C) were used as controls. After 24 hours of incubation, the antibiotics solutions were examined using HPLC. The results showed that after 24 hours of incubation, the kanamycin concentration of solution A decreased more than 25% relative to solution C. In contrast, the kanamycin concentration of solution B showed no significant change relative to solution C.

Example 8
Degradation of Erythromycin

*Saccharomyces cerevisiae* Hansen IFFI1211 cells were cultured in the presence of a series of alternating electric fields in the following sequence: the yeast cells were exposed to (1) an alternating electric field having a frequency of 73 MHz and a field strength of 48 mV/cm for 15 hours; (2) then to an alternating electric field having a frequency of 79 MHz and a field strength of 48 mV/cm for 15 hours; (3) then to an alternating electric field having a frequency of 88 MHz and a field strength of 48 mV/cm for 15 hours; (4) then to an alternating electric field having a frequency of 98 MHz and a field strength of 48 mV/cm for 15 hours; (5) then to an alternating electric field having a frequency of 73 MHz and a field strength of 200 mV/cm for 30 hours; (6) then to an alternating electric field having a frequency of 79 Mz and a field strength of 200 mV/cm for 30 hours, (7) then to an alternating electric field having a frequency of 88 MHz and a field strength of 200 mV/cm for 30 hours; and (8) finally to an alternating electric field having a frequency of 98 MHz and a field strength of 200 mV/cm for 30 hours.

To test the ability of the EMF-treated IFFI1211 cells to degrade erythromycin, waste water from a hospital was supplemented with erythromycin to reconstitute a solution containing the antibiotics at 100 mg/L. 0.1 ml of the EMF-treated IFFI1211 cells at a concentration higher than $10^8$ cells/ml was added to 100 L of the antibiotics solution and cultured at 28° C. for 24 hours (solution A). One hundred liters of the antibiotics solution containing the same number of non-treated cells (solution B) or containing no cells (solution C) were used as controls. After 24 hours of incubation, the antibiotics solutions were examined using HPLC. The results showed that after 24 hours of incubation, the erythromycin concentration of solution A decreased more than 27% relative to solution C. In contrast, the erythromycin concentration of solution B showed no significant change relative to solution C.

Example 9

Degradation of Spiramcyin

Saccharomyces cerevisiae Hansen IFFI1210 cells were cultured in the presence of a series of alternating electric fields in the following sequence: the yeast cells were exposed to (1) an alternating electric field having a frequency of 70 MHz and a field strength of 48 mV/cm for 15 hours; (2) then to an alternating electric field having a frequency of 77 MHz and a field strength of 48 mV/cm for 15 hours; (3) then to an alternating electric field having a frequency of 84 MHz and a field strength of 48 mV/cm for 15 hours; (4) then to an alternating electric field having a frequency of 93 MHz and a field strength of 48 mV/cm for 15 hours; (5) then to an alternating electric field having a frequency of 70 MHz and a field strength of 200 mV/cm for 30 hours; (6) then to an alternating electric field having a frequency of 77 MHz and a field strength of 200 mV/cm for 30 hours; (7) then to an alternating electric field having a frequency of 84 MHz and a field strength of 200 mV/cm for 30 hours; and (8) finally to an alternating electric field having a frequency of 93 MHz and a field strength of 200 mV/cm for 30 hours.

To test the ability of the EMF-treated IFFI1210 cells to degrade spiramycin, waste water from a hospital was supplemented with spiramycin to reconstitute a solution containing the antibiotics at 100 mg/L. 0.1 ml of the EMF-treated IFFI1210 cells at a concentration higher than $10^8$ cells/ml was added to 100 L of the antibiotics solution and cultured at 28° C. for 24 hours (solution A). One hundred liters of the antibiotics solution containing the same number of non-treated cells (solution B) or containing no cells (solution C) were used as controls. After 24 hours of incubation, the antibiotics solutions were examined using HPLC. The results showed that after 24 hours of incubation, the spiramycin concentration of solution A decreased more than 22% relative to solution C. In contrast, the spiramycin concentration of solution B showed no significant change relative to solution C.

Example 10

Degradation of Bacitracin

Saccharomyces cerevisiae Hansen IFFI1290 cells were cultured in the presence of a series of alternating electric fields in the following sequence: the yeast cells were exposed to (1) an alternating electric field having a frequency of 75 MHz and a field strength of 48 mV/cm for 15 hours; (2) then to an alternating electric field having a frequency of 78 MHz and a field strength of 48 mV/cm for 15 hours; (3) then to an alternating electric field having a frequency of 81 MHz and a field strength of 48 mV/cm for 15 hours; (4) then to an alternating electric field having a frequency of 95 MHz and a field strength of 48 mV/cm for 15 hours; (5) then to an alternating electric field having a frequency of 75 MHz and a field strength of 200 mV/cm for 30 hours; (6) then to an alternating electric field having a frequency of 78 MHz and a field strength of 200 mV/cm for 30 hours; (7) then to an alternating electric field having a frequency of 81 MHz and a field strength of 200 mV/cm for 30 hours; and (8) finally to an alternating electric field having a frequency of 95 MHz and a field strength of 200 mV/cm for 30 hours.

To test the ability of the EMF-treated IFFI1290 cells to degrade bacitracin, waste water from a hospital was supplemented with bacitracin to reconstitute a solution containing the antibiotics at 100 mg/L. 0.1 ml of the EMF-treated IFFI1290 cells at a concentration higher than $10^8$ cells/ml was added to 100 L of the antibiotics solution and cultured at 28° C. for 24 hours (solution A). One hundred liters of the antibiotics solution containing the same number of non-treated cells (solution B) or containing no cells (solution C) were used as controls. After 24 hours of incubation, the antibiotics solutions were examined using HPLC. The results showed that after 24 hours of incubation, the bacitracin concentration of solution A decreased more than 17% relative to solution C. In contrast, the bacitracin concentration of solution B showed no significant change relative to solution C.

Example 11

Degradation of Trichloromethane

Saccharomyces cerevisiae Hansen IFFI1413 cells were cultured in the presence of a series of alternating electric fields in the following sequence: the yeast cells were exposed to (1) an alternating electric field having a frequency of 82 MHz and a field strength of 98 mV/cm for 25 hours; (2) then to an alternating electric field having a frequency of 90 MHz and a field strength of 98 mV/cm for 25 hours; (3) then to an alternating electric field having a frequency of 82 MHz and a field strength of 274 mV/cm for 32 hours; and (4) finally to an alternating electric field having a frequency of 90 MHz and a field strength of 274 mV/cm for 12 hours.

To test the ability of the EMF-treated IFFI1413 cells to degrade trichioromethane, industrial waste water was supplemented with trichloromethane to reconstitute a solution containing the chemical at 100 mg/L. 0.1 ml of the EMF-treated IFFI11413 cells at a concentration higher than $10^8$ cells/ml was added to 100 L of the trichloromethane solution and cultured at 28° C. for 24 hours (solution A). One hundred liters of the trichloromethane solution containing the same number of non-treated cells (solution B) or containing no cells (solution C) were used as controls. After 24 hours of incubation, the trichloromethane solutions were examined using gas chromatography. The results showed that after 24 hours of incubation, the trichloromethane concentration of solution A decreased more than 29% relative to solution C. In contrast, the trichloromethane concentration of solution B showed no significant change relative to solution C.

Example 12
Degradation of Toluene

*Saccharomyces cerevisiae* Hansen IFFI1399 cells were cultured in the presence of a series of alternating electric fields in the following sequence: the yeast cells were exposed to (1) an alternating electric field having a frequency of 76 MHz and a field strength of 89 mV/cm for 20 hours; (2) then to an alternating electric field having a frequency of 80 MHz and a field strength of 89 mV/cm for 20 hours; (3) then to an alternating electric field having a frequency of 86 MHz and a field strength of 89 mV/cm for 20 hours; and (4) finally to an alternating electric field having a frequency of 96 MHz and a field strength of 89 mV/cm for 20 hours.

To test the ability of the EMF-treated IFFI1399 cells to degrade toluene, industrial waste water was supplemented with toluene to reconstitute a solution containing the chemical at 100 mg/L. 0.1 ml of the EMF-treated IFFI11399 cells at a concentration higher than $10^8$ cells/ml was added to 100 L of the toluene solution and cultured at 28° C. for 24 hours (solution A). One hundred liters of the toluene solution containing the same number of non-treated cells (solution B) or containing no cells (solution C) were used as controls. After 24 hours of incubation, the toluene solutions were examined using gas chromatography or HPLC. The results showed that after 24 hours of incubation, the toluene concentration of solution A decreased more than 32% relative to solution C. In contrast, the toluene concentration of solution B showed no significant change relative to solution C.

Example 13
Degradation of p-Xylene

*Saccharomyces cerevisiae* Hansen IFFI1336 cells were cultured in the presence of a series of alternating electric fields in the following sequence: the yeast cells were exposed to (1) an alternating electric field having a frequency of 72 MHz and a field strength of 93 mV/cm for 20 hours; (2) then to an alternating electric field having a frequency of 80 MHz and a field strength of 93 mV/cm for 20 hours; (3) then to an alternating electric field having a frequency of 88 MHz and a field strength of 93 mV/cm for 20 hours; and (4) finally to an alternating electric field having a frequency of 98 MHz and a field strength of 93 mV/cm for 20 hours.

To test the ability of the EMF-treated IFFI1336 cells to degrade p-xylene, industrial waste water was supplemented with p-xylene to reconstitute a solution containing the chemical at 100 mg/L. 0.1 ml of the EMF-treated IFFI11336 cells at a concentration higher than $10^8$ cells/ml was added to 100 L of the xylene solution and cultured at 28° C. for 24 hours (solution A). One hundred liters of the xylene solution containing the same number of non-treated cells (solution B) or containing no cells (solution C) were used as controls. After 24 hours of incubation, the xylene solutions were examined using gas chromatography or HPLC. The results showed that after 24 hours of incubation, the xylene concentration of solution A decreased more than 24% relative to solution C. In contrast, the xylene concentration of solution B showed no significant change relative to solution C.

Example 14
Degradation of Benzaldehyde

*Saccharomyces cerevisiae* Hansen IFFI1331 cells were cultured in the presence of a series of alternating electric fields in the following sequence: the yeast cells were exposed to (1) an alternating electric field having a frequency of 78 MHz and a field strength of 130 mV/cm for 30 hours; (2) then to an alternating electric field having a frequency of 86 MHz and a field strength of 130 mV/cm for 30 hours; (3) then to an alternating electric field having a frequency of 94 MHz and a field strength of 130 mV/cm for 30 hours; and (4) finally to an alternating electric field having a frequency of 96 MHz and a field strength of 130 mV/cm for 30 hours.

To test the ability of the EMF-treated IFFI1331 cells to degrade benzaldehyde, industrial waste water was supplemented with benzaldehyde to reconstitute a solution containing the chemical at 100 mg/L. 0.1 ml of the EMF-treated IFFI11331 cells at a concentration higher than $10^8$ cells/ml was added to 100 L of the benzaldehyde solution and cultured at 28° C. for 24 hours (solution A). One hundred liters of the benzaldehyde solution containing the same number of non-treated cells (solution B) or containing no cells (solution C) were used as controls. After 24 hours of incubation, the benzaldehyde solutions were examined using gas chromatography or HPLC. The results showed that after 24 hours of incubation, the benzaldehyde concentration of solution A decreased more than 34% relative to solution C. In contrast, the benzaldehyde concentration of solution B showed no significant change relative to solution C.

Example 15
Degradation of Propylaldehyde

*Saccharomyces cerevisiae* Hansen IFFI1396 cells were cultured in the presence of a series of alternating electric fields in the following sequence: the yeast cells were exposed to (1) an alternating electric field having a frequency of 76 MHz and a field strength of 103 mV/cm for 20 hours; (2) then to an alternating electric field having a frequency of 8 MHz and a field strength of 103 mV/cm for 20 hours; (3) then to an alternating electric field having a frequency of 96 MHz and a field strength of 103 mV/cm for 20 hours; and (4) finally to an alternating electric field having a frequency of 98 MHz and a field strength of 103 mV/cm for 30 hours.

To test the ability of the EMF-treated IFFI1396 cells to degrade propylaldehyde, industrial waste water was supplemented with propylaldehyde to reconstitute a solution containing the chemical at 100 mg/L. 0.1 ml of the EMF-treated IFFI11396 cells at a concentration higher than $10^8$ cells/ml was added to 100 L of the propylaldehyde solution and cultured at 28° C. for 24 hours (solution A). One hundred liters of the propylaldehyde solution containing the same number of non-treated cells (solution B) or containing no cells (solution C) were used as controls. After 24 hours of incubation, the propylaldehyde solutions were examined using gas chromatography or HPLC. The results showed that after 24 hours of incubation, the propylaldehyde concentration of solution A decreased more than 19% relative to solution C. In contrast, the propylaldehyde concentration of solution B showed no significant change relative to solution C.

Example 16
Degradation of Enanthaldehyde

*Saccharomyces cerevisiae* Hansen IFFI1310 cells were cultured in the presence of a series of alternating electric fields in the following sequence: the yeast cells were exposed to (1) an alternating electric field having a frequency of 74 MHz and a field strength of 126 mV/cm for 40 hours; (2) then to an alternating electric field having a frequency of 82 MHz and a field strength of 126 mV/cm for 20 hours; (3) then to an alternating electric field having a frequency of 90 MHz and a field strength of 126 mV/cm for 30 hours; and (4) finally to an alternating electric field having a frequency of 98 MHz and a field strength of 126 mV/cm for 40 hours.

To test the ability of the EMF-treated IFFI1310 cells to degrade enanthaldehyde, industrial waste water was supplemented with enanthaldehyde to reconstitute a solution containing the chemical at 100 mg/L. 0.1 ml of the EMF-treated IFFI1310 cells at a concentration higher than $10^8$ cells/ml was added to 100 L of the enanthaldehyde solution and cultured at 28° C. for 24 hours (solution A). One hundred liters of the enanthaldehyde solution containing the same number of non-treated cells (solution B) or containing no cells (solution C) were used as controls. After 24 hours of incubation, the enanthaldehyde solutions were examined using gas chromatography or HPLC. The results showed that after 24 hours of incubation, the enanthaldehyde concentration of solution A decreased more than 22% relative to solution C. In contrast, the enanthaldehyde concentration of solution B showed no significant change relative to solution C.

Example 17

Degradation of m-Dichlorobenzene

*Saccharomyces cerevisiae* Hansen IFFI1331 cells were cultured in the presence of a series of alternating electric fields in the following sequence: the yeast cells were exposed to (1) an alternating electric field having a frequency of 72 MHz and a field strength of 107 mV/cm for 20 hours; (2) then to an alternating electric field having a frequency of 80 MHz and a field strength of 107 mV/cm for 10 hours; (3) then to an alternating electric field having a frequency of 90 MHz and a field strength of 107 mV/cm for 30 hours; and (4) finally to an alternating electric field having a frequency of 94 MHz and a field strength of 107 mV/cm for 40 hours.

To test the ability of the EMF-treated IFFI1331 cells to degrade m-dichlorobenzene, waste water was supplemented with m-dichlorobenzene to reconstitute a solution containing the chemical at 100 mg/L. 0.1 ml of the EMF-treated IFFI1331 cells at a concentration higher than $10^8$ cells/ml was added to 100 L of the m-dichlorobenzene solution and cultured at 28° C. for 24 hours (solution A). One hundred liters of the m-dichlorobenzene solution containing the same number of non-treated cells (solution B) or containing no cells (solution C) were used as controls. After 24 hours of incubation, the m-dichlorobenzene solutions were examined using gas chromatography or HPLC. The results showed that after 24 hours of incubation, the m-dichlorobenzene concentration of solution A decreased more than 26% relative to solution C. In contrast, the m-dichlorobenzene concentration of solution B showed no significant change relative to solution C.

Example 18

Degradation of Acetophenone

*Saccharomyces cerevisiae* Hansen IFFI1311 cells were cultured in the presence of a series of alternating electric fields in the following sequence: the yeast cells were exposed to (1) an alternating electric field having a frequency of 76 MHz and a field strength of 124 mV/cm for 20 hours; (2) then to an alternating electric field having a frequency of 82 MHz and a field strength of 124 mV/cm for 30 hours; (3) then to an alternating electric field having a frequency of 90 MHz and a field strength of 124 mV/cm for 40 hours; and (4) finally to an alternating electric field having a frequency of 98 MHz and a field strength of 124 mV/cm for 20 hours.

To test the ability of the EMF-treated IFFI1311 cells to degrade acetophenone, waste water was supplemented with acetophenone to reconstitute a solution containing the chemical at 100 mg/L. 0.1 ml of the EMF-treated IFFI1311 cells at a concentration higher than $10^8$ cells/ml was added to 100 L of the acetophenone solution and cultured at 28° C. for 24 hours (solution A). One hundred liters of the acetophenone solution containing the same number of non-treated cells (solution B) or containing no cells (solution C) were used as controls. After 24 hours of incubation, the acetophenone solutions were examined using gas chromatography or HPLC. The results showed that after 24 hours of incubation, the acetophenone concentration of solution A decreased more than 11% relative to solution C. In contrast, the acetophenone concentration of solution B showed no significant change relative to solution C.

Example 19

Degradation of Arsanilic Acid

*Saccharomyces cerevisiae* Hansen IFFI1336 cells were cultured in the presence of a series of alternating electric fields in the following sequence: the yeast cells were exposed to (1) an alternating electric field having a frequency of 78 MHz and a field strength of 133 mV/cm for 30 hours; (2) then to an alternating electric field having a frequency of 88 MHz and a field strength of 133 mV/cm for 40 hours; (3) then to an alternating electric field having a frequency of 92 MHz and a field strength of 133 mV/cm for 30 hours; and (4) finally to an alternating electric field having a frequency of 96 MHz and a field strength of 133 mV/cm for 30 hours.

To test the ability of the EMF-treated IFFI1336 cells to degrade arsanilic acid, waste water was supplemented with arsanilic acid to reconstitute a solution containing the chemical at 100 mg/L. 0.1 ml of the EMF-treated IFFI1336 cells at a concentration higher than $10^8$ cells/ml was added to 100 L of the arsanilic acid solution and cultured at 28° C. for 24 hours (solution A). One hundred liters of the arsanilic acid solution containing the same number of non-treated cells (solution B) or containing no cells (solution C) were used as controls. After 24 hours of incubation, the arsanilic acid solutions were examined using gas chromatography or HPLC. The results showed that after 24 hours of incubation, the arsanilic acid concentration of solution A decreased more than 13% relative to solution C. In contrast, the arsanilic acid concentration of solution B showed no significant change relative to solution C.

Example 20

Degradation of Roxarsone

*Saccharomyces cerevisiae* Hansen IFFI1338 cells were cultured in the presence of a series of alternating electric fields in the following sequence: the yeast cells were exposed to (1) an alternating electric field having a frequency of 78 MHz and a field strength of 110 mV/cm for 10 hours; (2) then to an alternating electric field having a frequency of 92 MHz and a field strength of 110 mV/cm for 10 hours; (3) then to an alternating electric field having a frequency of 78 MHz and a field strength of 213 mV/cm for 30 hours; and (4) finally to an alternating electric field having a frequency of 92 MHz and a field strength of 213 mV/cm for 30 hours.

To test the ability of the EMF-treated IFFI1338 cells to degrade roxarsone, waste water was supplemented with roxarsone to reconstitute a solution containing the chemical at 100 mg/L. 0.1 ml of the EMF-treated IFFI1338 cells at a concentration higher than $10^8$ cells/ml was added to 100 L of the roxarsone solution and cultured at 28° C. for 24 hours (solution A). One hundred liters of the roxarsone solution containing the same number of non-treated cells (solution B) or containing no cells (solution C) were used as controls. After 24 hours of incubation, the roxarsone solutions were examined using gas chromatography or HPLC. The results showed that after 24 hours of incubation, the roxarsone concentration of solution A decreased more than 13% relative to solution C. In contrast, the roxarsone concentration of solution B showed no significant change relative to solution C.

Example 21
Degradation of Furazolidonum

Saccharomyces cerevisiae Hansen IFFI1413 cells were cultured in the presence of a series of alternating electric fields in the following sequence: the yeast cells were exposed to (1) an alternating electric field having a frequency of 74 MHz and a field strength of 98 mV/cm for 30 hours; (2) then to an alternating electric field having a frequency of 76 MHz and a field strength of 98 mV/cm for 20 hours; (3) then to an alternating electric field having a frequency of 86 MHz and a field strength of 98 mV/cm for 30 hours; and (4) finally to an alternating electric field having a frequency of 94 MHz and a field strength of 98 mV/cm for 30 hours.

To test the ability of the EMF-treated IFFI1413 cells to degrade furazolidonum, waste water was supplemented with furazolidonum to reconstitute a solution containing the chemical at 100 mg/L. 0.1 ml of the EMF-treated IFFI1413 cells at a concentration higher than $10^8$ cells/ml was added to 100 L of the furazolidonum solution and cultured at 28° C. for 24 hours (solution A). One hundred liters of the furazolidonum solution containing the same number of nontreated cells (solution B) or containing no cells (solution C) were used as controls. After 24 hours of incubation, the furazolidonum solutions were examined using gas chromatography or HPLC. The results showed that after 24 hours of incubation, the furazolidonum concentration of solution A decreased more than 10% relative to solution C. In contrast, the furazolidonum concentration of solution B showed no significant change relative to solution C.

Example 22
Degradation of Decoquinate

Saccharomyces cerevisiae Hansen IFFI1411 cells were cultured in the presence of a series of alternating electric fields in the following sequence: the yeast cells were exposed to (1) an alternating electric field having a frequency of 78 MHz and a field strength of 112 mV/cm for 30 hours; (2) then to an alternating electric field having a frequency of 82 MHz and a field strength of 112 mV/cm for 30 hours; (3) then to an alternating electric field having a frequency of 86 MHz and a field strength of 112 mV/cm for 30 hours; and (4) finally to an alternating electric field having a frequency of 94 MHz and a field strength of 112 mV/cm for 20 hours.

To test the ability of the EMF-treated IFFI1411 cells to degrade decoquinate, waste water was supplemented with decoquinate to reconstitute a solution containing the chemical at 100 mg/L. 0.1 ml of the EMF-treated IFFI1411 cells at a concentration higher than $10^8$ cells/ml was added to 100 L of the decoquinate solution and cultured at 28° C. for 24 hours (solution A). One hundred liters of the decoquinate solution containing the same number of non-treated cells (solution B) or containing no cells (solution C) were used as controls. After 24 hours of incubation, the decoquinate solutions were examined using gas chromatography or HPLC. The results showed that after 24 hours of incubation, the decoquinate concentration of solution A decreased more than 17% relative to solution C. In contrast, the decoquinate concentration of solution B showed no significant change relative to solution C.

Example 23
Degradation of Trichlorphonum

Saccharomyces cerevisiae Hansen IFFI1211 cells were cultured in the presence of a series of alternating electric fields in the following sequence: the yeast cells were exposed to (1) an alternating electric field having a frequency of 74 MHz and a field strength of 219 mV/cm for 30 hours; (2) then to an alternating electric field having a frequency of 86 MHz and a field strength of 219 mV/cm for 20 hours; (3) then to an alternating electric field having a frequency of 96 MHz and a field strength of 219 mV/cm for 30 hours; and (4) finally to an alternating electric field having a frequency of 98 MHz and a field strength of 219 mV/cm for 20 hours.

To test the ability of the EMF-treated IFFI1211 cells to degrade trichlorphonum, waste water was supplemented with trichlorphonum to reconstitute a solution containing the chemical at 100 mg/L. 0.1 ml of the EMF-treated IFFI1211 cells at a concentration higher than $10^8$ cells/mi was added to 100 L of the trichlorphonum solution and cultured at 28° C. for 24 hours (solution A). One hundred liters of the trichlorphonum solution containing the same number of nontreated cells (solution B) or containing no cells (solution C) were used as controls. After 24 hours of incubation, the trichlorphonum solutions were examined using gas chromatography or HPLC. The results showed that after 24 hours of incubation, the trichlorphonum concentration of solution A decreased more than 15% relative to solution C. In contrast, the trichlorphonum concentration of solution B showed no significant change relative to solution C.

Example 24
Degradation of Dinitomidum and Zoalene

Saccharomyces cerevisiae Hansen IFFI1063 cells were cultured in the presence of a series of alternating electric fields in the following sequence: the yeast cells were exposed to (1) an alternating electric field having a frequency of 76 MHz and a field strength of 202 mV/cm for 30 hours; (2) then to an alternating electric field having a frequency of 82 MHz and a field strength of 202 mV/cm for 30 hours; (3) then to an alternating electric field having a frequency of 90 MHz and a field strength of 202 mV/cm for 20 hours; and (4) finally to an alternating electric field having a frequency of 96 MHz and a field strength of 202 mV/cm for 20 hours.

To test the ability of the EMF-treated EFFI1063 cells to degrade dinitomidum, waste water was supplemented with dinitomidum to reconstitute a solution containing the chemical at 100 mg/L. 0.1 ml of the EMF-treated IFFI1063 cells at a concentration higher than $10^8$ cells/ml was added to 100 L of the dinitomidum solution and cultured at 28° C. for 24 hours (solution A). One hundred liters of the dinitomidum solution containing the same number of non-treated cells (solution B) or containing no cells (solution C) were used as controls. After 24 hours of incubation, the dinitomidum solutions were examined using gas chromatography or HPLC. The results showed that after 24 hours of incubation, the dinitomidum concentration of solution A decreased more than 26% relative to solution C. In contrast, the dinitomidum concentration of solution B showed no significant change relative to solution C. The same method can be used to assess the zoalene-degrading ability of activated yeast cells.

Example 25
Degradation of Dodecane

Saccharomyces cerevisiae Hansen IFFI1213 cells were cultured in the presence of a series of alternating electric fields in the following sequence: the yeast cells were exposed to (1) an alternating electric field having a frequency of 72 MHz and a field strength of 168 mV/cm for 30 hours; (2) then to an alternating electric field having a frequency of 80 MHz and a field strength of 168 mV/cm for 20 hours; (3) then to an alternating electric field having a frequency of 90 MHz and a field strength of 168 mV/cm for 30 hours; and (4) finally to an alternating electric field having a frequency of 98 MHz and a field strength of 168 mV/cm for 30 hours.

To test the ability of the EMF-treated IFFI1213 cells to degrade dodecane, waste water was supplemented with dodecane to reconstitute a solution containing the chemical at 100 mg/L. 0.1 ml of the EMF-treated IFFI1213 cells at a concentration higher than $10^8$ cells/ml was added to 100 L of the dodecane solution and cultured at 28° C. for 24 hours (solution A). One hundred liters of the dodecane solution containing the same number of non-treated cells (solution B) or containing no cells (solution C) were used as controls. After 24 hours of incubation, the dodecane solutions were examined using gas chromatography or HPLC. The results showed that after 24 hours of incubation, the dodecane concentration of solution A decreased more than 21% relative to solution C. In contrast, the dodecane concentration of solution B showed no significant change relative to solution C.

Example 26

Degradation of Nonadecane

*Saccharomyces cerevisiae* Hansen IFFI1270 cells were cultured in the presence of a series of alternating electric fields in the following sequence: the yeast cells were exposed to (1) an alternating electric field having a frequency of 80 MHz and a field strength of 138 mV/cm for 30 hours; (2) then to an alternating electric field having a frequency of 82 MHz and a field strength of 138 mV/cm for 20 hours; (3) then to an alternating electric field having a frequency of 94 MHz and a field strength of 138 mV/cm for 24 hours, and (4) finally to an alternating electric field having a frequency of 98 MHz and a field strength of 138 mV/cm for 30 hours.

To test the ability of the EMF-treated IFFI1270 cells to degrade nonadecane, waste water was supplemented with nonadecane to reconstitute a solution containing the chemical at 100 mg/L. 0.1 ml of the EMF-treated IFFI1270 cells at a concentration higher than $10^8$ cells/ml was added to 100 L of the nonadecane solution and cultured at 28° C. for 24 hours (solution A). One hundred liters of the nonadecane solution containing the same number of non-treated cells (solution B) or containing no cells (solution C) were used as controls. After 24 hours of incubation, the nonadecane solutions were examined using gas chromatography or HPLC. The results showed that after 24 hours of incubation, the nonadecane concentration of solution A decreased more than 23% relative to solution C. In contrast, the nonadecane concentration of solution B showed no significant change relative to solution C.

Example 27

Degradation of Octacosane

*Saccharomyces cerevisiae* Hansen IFFI1293 cells were cultured in the presence of a series of alternating electric fields in the following sequence: the yeast cells were exposed to (1) an alternating electric field having a frequency of 76 MHz and a field strength of 138 mV/cm for 24 hours; (2) then to an alternating electric field having a frequency of 84 MHz and a field strength of 138 mV/cm for 24 hours; (3) then to an alternating electric field having a frequency of 96 MHz and a field strength of 138 mV/cm for 20 hours; and (4) finally to an alternating electric field having a frequency of 98 MHz and a field strength of 138 mV/cm for 40 hours.

To test the ability of the EMF-treated IFFI1293 cells to degrade octacosane, waste water was supplemented with octacosane to reconstitute a solution containing the chemical at 100 mg/L. 0.1 ml of the EMF-treated EFFI1293 cells at a concentration higher than $10^8$ cells/ml was added to 100 L of the octacosane solution and cultured at 28° C. for 24 hours (solution A). One hundred liters of the octacosane solution containing the same number of non-treated cells (solution B) or containing no cells (solution C) were used as controls. After 24 hours of incubation, the octacosane solutions were examined using gas chromatography or HPLC. The results showed that after 24 hours of incubation, the octacosane concentration of solution A decreased more than 20% relative to solution C. In contrast, the octacosane concentration of solution B showed no significant change relative to solution C.

While a number of embodiments of this invention have been set forth, it is apparent that the basic constructions may be altered to provide other embodiments which utilize the compositions and methods of this invention.

What is claimed is:

1. A composition comprising a plurality of yeast cells, wherein said plurality of yeast cells are characterized by a substantial increase in their capability to degrade an antibiotic or an organic solvent in a culture medium as a result of having been cultured in the presence of an alternating electric field having a frequency in the range of 70 to 100 MHz and a field strength in the range of 0.5 to 350 mV/cm, as compared to yeast cells not having been so cultured.

2. The composition of claim 1, wherein said yeast cells are cells of the species *Saccharomyces cerevisiae, Saccharomyces carlsbergensis, Saccharomyces rouxii, Saccharomyces willianus,* or *Candida utilis.*

3. The composition of claim 1, wherein said yeast cells are derived from cells of the strain deposited at The China General Microbiological Culture Collection Center with an accession number selected from the group consisting of AS2.4, AS2.14, AS2.416, AS2.430, AS2.593, IFFI1002, IFFI1006, IFFI1043, IFFI1045, IFFI1048, IFFI1063, IFFI1059, IFFI1206, IFFI1209, IFFI1210, IFFI1211, IFFI1213, IFFI1215, IFFI1220, IFFI1221, IFFI1224, IFFI1248, IFFI1270, IFFI1290, IFFI1291, IFFI1293, IFFI1297, IFFI1301, IFFI1302, IFFI1310, IFFI1311, IFFI1331, IFFI1335, IFFI1336, IFFI1338, IFFI1339, IFFI1340, IFFI1345, IFFI1396, IFFI1399, IFFI1411, IFFI1413, AS2.293, AS2.377, AS2.444, AS2.178, and AS2.120.

4. The composition of claim 1, wherein said antibiotic is penicillin.

5. The composition of claim 4, wherein said field strength is in the range of 30–220 mV/cm.

6. The composition of claim 1, wherein said antibiotic is chlortetracycline.

7. The composition of claim 6, wherein said field strength is in the range of 30–230 mV/cm.

8. The composition of claim 1, wherein said antibiotic is oxytetracycline.

9. The composition of claim 8, wherein said field strength is in the range of 30–250 mV/cm.

10. The composition of claim 1, wherein said antibiotic is doxycycline.

11. The composition of claim 10, wherein said field strength is in the range of 30–250 mV/cm.

12. The composition of claim 1, wherein said antibiotic is tetracycline.

13. The composition of claim 12, wherein said field strength is in the range of 30–230 mV/cm.

14. The composition of claim 1, wherein said antibiotic is streptomycin.

15. The composition of claim 14, wherein said field strength is in the range of 30–230 mV/cm.

16. The composition of claim 1, wherein said antibiotic is kanamycin.

17. The composition of claim 16, wherein said field strength is in range of 30–230 mV/cm.

18. The composition of claim 1, wherein said antibiotic is erythromycin.

19. The composition of claim 18, wherein said field strength is in the range of 30–250 mV/cm.

20. The composition of claim 1, wherein said antibiotic is spiramycin.

21. The composition of claim 20, wherein said field strength is in the range of 30–230 mV/cm.

22. The composition of claim 1, wherein said antibiotic is bacitracin.

23. The composition of claim 22, wherein said field strength is in the range of 30–230 mV/cm.

24. The composition of claim 1, wherein said organic solvent is trichloromethane.

25. The composition of claim 24, wherein said field strength is in the range of 90–280 mV/cm.

26. The composition of claim 1, wherein said organic solvent is toluene or ethylbenzene.

27. The composition of claim 26, wherein said field strength is in the range of 80–280 mV/cm.

28. The composition of claim 1, wherein said organic solvent is p-xylene.

29. The composition of claim 28, wherein said field strength is in the range of 80–280 mV/cm.

30. The composition of claim 1, wherein said organic solvent is furazolidonum.

31. The composition of claim 30, wherein said field strength is in the range of 80–280 mV/cm.

32. The composition of claim 1, wherein said organic solvent is decoquinate.

33. The composition of claim 32, wherein said field strength is in the range of 90–280 mV/cm.

34. The composition of claim 1, wherein said organic solvent is benzaldehyde.

35. The composition of claim 34, wherein said field strength is in the range of 120–280 mV/cm.

36. The composition of claim 1, wherein said organic solvent is propylaldehyde.

37. The composition of claim 36, wherein said field strength is in the range of 100–200 mV/cm.

38. The composition of claim 1, wherein said organic solvent is enanthaldehyde.

39. The composition of claim 38, wherein said field strength is in the range of 110–280 mV/cm.

40. The composition of claim 1, wherein said organic solvent is m-dichlorobenzene.

41. The composition of claim 40, wherein said field strength is in the range of 100–220 mV/cm.

42. The composition of claim 1, wherein said organic solvent is acetophenone.

43. The composition of claim 42, wherein said field strength is in the range of 116–225 mV/cm.

44. The composition of claim 1, wherein said organic solvent is arsanilic acid.

45. The composition of claim 44, wherein said field strength is in the range of 90–190 mV/cm.

46. The composition of claim 1, wherein said organic solvent is roxarsone.

47. The composition of claim 46, wherein said field strength is in the range of 100–190 mV/cm.

48. The composition of claim 1, wherein said organic solvent is dodecane.

49. The composition of claim 48, wherein said field strength is in the range of 160–300 mV/cm.

50. The composition of claim 1, wherein said organic solvent is nonadecane.

51. The composition of claim 50, wherein said field strength is in the range of 120–300 mV/cm.

52. The composition of claim 1, wherein said organic solvent is octacosane.

53. The composition of claim 52, wherein said field strength is in the range of 120–300 mV/cm.

54. The composition of claim 1, wherein said organic solvent is trichlorphonum.

55. The composition of claim 54, wherein said field strength is in the range of 200–300 mV/cm.

56. The composition of claim 1, wherein said organic solvent is dinitomidum or zoalene.

57. The composition of claim 56, wherein said field strength is in the range of 130–310 mV/cm.

58. A composition comprising a plurality of yeast cells, wherein said plurality of yeast cells are characterized by a substantial increase in their capability to degrade trichloromethane in a culture medium as a result of having been cultured in the presence of an alternating electric field having a frequency in the range of 126 to 142 MHz and a field strength in the range of 90 to 280 mV/cm, as compared to yeast cells not having been so cultured.

59. A composition comprising a plurality of yeast cells, wherein said plurality of yeast cells are characterized by a substantial increase in their capability to degrade toluene or ethylbenzene in a culture medium as a result of having been cultured in the presence of an alternating electric field having a frequency in the range of 52 to 70 MHz and a field strength in the range of 80 to 280 mV/cm, as compared to yeast cells not having been so cultured.

60. A composition comprising a plurality of yeast cells, wherein said plurality of yeast cells are characterized by a substantial increase in their capability to degrade p-xylene in a culture medium as a result of having been cultured in the presence of an alternating electric field having a frequency in the range of 30 to 50 MHz and a field strength in the range of 80 to 280 mV/cm, as compared to yeast cells not having been so cultured.

61. A composition comprising a plurality of yeast cells, wherein said plurality of yeast cells are characterized by a substantial increase in their capability to degrade furazolidonum in a culture medium as a result of having been cultured in the presence of an alternating electric field having a frequency in the range of 200 to 220 MHz and a field strength in the range of 80 to 280 mV/cm, as compared to yeast cells not having been so cultured.

62. A composition comprising a plurality of yeast cells, wherein said plurality of yeast cells are characterized by a substantial increase in their capability to degrade decoquinate in a culture medium as a result of having been cultured in the presence of an alternating electric field having a frequency in the range of 213 to 229 MHz and a field strength in the range of 90 to 280 mV/cm, as compared to yeast cells not having been so cultured.

63. A composition comprising a plurality of yeast cells, wherein said plurality of yeast cells are characterized by a substantial increase in their capability to degrade benzaldehyde in a culture medium as a result of having been cultured in the presence of an alternating electric field having a frequency in the range of 133 to 151 MHz and a field strength in the range of 120 to 280 mV/cm, as compared to yeast cells not having been so cultured.

64. A composition comprising a plurality of yeast cells, wherein said plurality of yeast cells are characterized by a substantial increase in their capability to degrade propylaldehyde in a culture medium as a result of having been cultured in the presence of an alternating electric field having a frequency in the range of 145 to 162 MHz and a field strength in the range of 100 to 200 mV/cm, as compared to yeast cells not having been so cultured.

65. A composition comprising a plurality of yeast cells, wherein said plurality of yeast cells are characterized by a substantial increase in their capability to degrade enanthaldehyde in a culture medium as a result of having been cultured in the presence of an alternating electric field having a frequency in the range of 156 to 176 MHz and a field strength in the range of 110 to 280 mV/cm, as compared to yeast cells not having been so cultured.

66. A composition comprising a plurality of yeast cells, wherein said plurality of yeast cells are characterized by a substantial increase in their capability to degrade m-dichlorobenzene in a culture medium as a result of having been cultured in the presence of an alternating electric field having a frequency in the range of 163 to 183 MHz and a field strength in the range of 100 to 220 mV/cm, as compared to yeast cells not having been so cultured.

67. A composition comprising a plurality of yeast cells, wherein said plurality of yeast cells are characterized by a substantial increase in their capability to degrade acetophenone in a culture medium as a result of having been cultured in the presence of an alternating electric field having a frequency in the range of 175 to 191 MHz and a field strength in the range of 116 to 225 mV/cm, as compared to yeast cells not having been so cultured.

68. A composition comprising a plurality of yeast cells, wherein said plurality of yeast cells are characterized by a substantial increase in their capability to degrade arsanilic acid in a culture medium as a result of having been cultured in the presence of an alternating electric field having a frequency in the range of 183 to 205 MHz and a field strength in the range of 90 to 190 mV/cm, as compared to yeast cells not having been so cultured.

69. A composition comprising a plurality of yeast cells, wherein said plurality of yeast cells are characterized by a substantial increase in their capability to degrade roxarsone in a culture medium as a result of having been cultured in the presence of an alternating electric field having a frequency in the range of 114 to 128 MHz and a field strength in the range of 100 to 190 mV/cm, as compared to yeast cells not having been so cultured.

70. A composition comprising a plurality of yeast cells, wherein said plurality of yeast cells are characterized by a substantial increase in their capability to degrade dodecane in a culture medium as a result of having been cultured in the presence of an alternating electric field having a frequency in the range of 244 to 264 MHz and a field strength in the range of 160 to 300 mV/cm, as compared to yeast cells not having been so cultured.

71. A composition comprising a plurality of yeast cells, wherein said plurality of yeast cells are characterized by a substantial increase in their capability to degrade nonadecane or octacosane in a culture medium as a result of having been cultured in the presence of an alternating electric field having a frequency in the range of 252 to 278 MHz and a field strength in the range of 120 to 300 mV/cm, as compared to yeast cells not having been so cultured.

72. A composition comprising a plurality of yeast cells, wherein said plurality of yeast cells are characterized by a substantial increase in their capability to degrade trichlorophorum in a culture medium as a result of having been cultured in the presence of an alternating electric field having a frequency in the range of 220 to 250 MHz and a field strength in the range of 200 to 300 mV/cm, as compared to yeast cells not having been so cultured.

73. A composition comprising a plurality of yeast cells, wherein said plurality of yeast cells are characterized by a substantial increase in their capability to degrade dinitomidum or zoalene in a culture medium as a result of having been cultured in the presence of an alternating electric field having a frequency in the range of 220 to 250 MHz and a field strength in the range of 130 to 310 mV/cm, as compared to yeast cells not having been so cultured.

74. A method of preparing a yeast composition, comprising culturing a plurality of yeast cells in the presence of an alternating electric field having a frequency in the range of 70 to 100 MHz and a field strength in the range of 0.5 to 350 mV/cm, wherein said plurality of yeast cells are characterized by a substantial increase in their capability to degrade an antibiotic or an organic solvent in a culture medium as a result of said culturing as compared to yeast cells not having been so cultured.

* * * * *

UNITED STATES PATENT AND TRADEMARK OFFICE
CERTIFICATE OF CORRECTION

PATENT NO. : 6,391,618 B1  Page 1 of 1
DATED : May 21, 2002
INVENTOR(S) : Ling Yuk Cheung It is certified that error appears in the above-identified patent and that said Letters Patent is hereby corrected as shown below:

Column 7,
Line 34, change "120-290" to -- 120-280 --.
Line 34, change "120-100" to -- 120-300 --.

Column 11,
Line 43, change "8 MHz" to -- 88 MHz --.

Column 16,
Line 50, change "12 hours" to -- 32 hours --.

Column 18,
Line 31, change "8 MHz" to -- 88 MHz --.

Signed and Sealed this

Seventeenth Day of February, 2004

JON W. DUDAS
*Acting Director of the United States Patent and Trademark Office*